United States Patent [19]

Whitney

[11] Patent Number: 4,597,384
[45] Date of Patent: Jul. 1, 1986

[54] SEQUENTIAL COMPRESSION SLEEVE

[75] Inventor: John K. Whitney, Dorado Beach, P.R.

[73] Assignee: Gaymar Industries, Inc., Orchard Park, N.Y.

[21] Appl. No.: 626,015

[22] Filed: Jun. 29, 1984

[51] Int. Cl.$^4$ ............................................. A61H 7/00
[52] U.S. Cl. ........................ 128/24 R; 128/DIG. 20; 128/64
[58] Field of Search ......... 128/38, 40, 24 R, DIG. 20, 128/64, 24.1, 39

[56] References Cited

U.S. PATENT DOCUMENTS

| | | | |
|---|---|---|---|
| 3,094,116 | 6/1963 | Logan et al. | 128/24 R |
| 3,654,919 | 4/1972 | Birtwell | 128/40 |
| 3,862,629 | 1/1975 | Rotta | 128/64 |
| 3,920,006 | 11/1975 | Lapidus | 128/24.1 |
| 4,013,069 | 3/1977 | Hasty | 128/24 R |
| 4,402,312 | 9/1983 | Villari et al. | 128/24 R |

FOREIGN PATENT DOCUMENTS 2511241  2/1983  France ................ 128/64

*Primary Examiner*—Clifford D. Crowder
*Assistant Examiner*—Tonya Eckstine
*Attorney, Agent, or Firm*—Witherspoon & Hargest

[57] ABSTRACT

A sleeve device for encasing and applying successive compressive pressures against a patient's limb from a source of pressurized fluid, the sleeve has a plurality of laterally extending separate fluid pressure members progressively arranged longitudinally along the sleeve from a lower portion of the encased limb to the upper portion thereof, the adjacent lateral edge portions of adjacent pressure members are curved upwardly and then downwardly in unison whereby the respective contiguous edges thereof follow each other so that when pressure is successively applied from the lowermost pressure member upward there will never be a continuous circumferential pressure gap on any lateral circular portion of the encircled limb and further wherein the successive pressurization of each pressure member from the lowermost heartward produces a plurality of circumferentially spaced radially inward maximum and minimum forces interdigitated with successive pressure members having similar maximum and minimum forces to produce a smooth stasis free blood flow in the area treated.

5 Claims, 6 Drawing Figures

SEQUENTIAL COMPRESSION SLEEVE

BACKGROUND AND OBJECTS OF THE INVENTION

The present invention relates to therapeutic and prophylactic devices for the alleviation of deep venous thrombosis by mechanical as opposed to chemical means. Deep venous thrombosis (DVT) is a condition in which clotting of venous blood occurs generally in the lower extremities due to lack of sufficient muscular activity in the lower extremities. Thus it is important that the velocity of blood flow in the patient's extremities be maintained at the requisite level in order to prevent pooling of blood in such extremities so that stasis of blood will not develop. This is particularly important since it is well known that stasis of blood is a significant cause leading to the formation of thrombi in the patient's extremities which could ultimately cause the death of the patient.

Devices are presently in use for the purpose of increasing blood velocity to prevent problems set forth above. Many of these devices comprise compression sleeves which fit over and around the limb requiring care. Fluid pressure producing means are provided for sequentially inflating the compression sleeve and allowing for a simultaneous deflation of all sleeve components.

Applicant's U.S. Pat. No. 4,453,538 which is entitled "Medical Apparatus" and issued on June 12, 1984, is hereby and herewith incorporated for all of its disclosure into this application. Among other features this patent describes a flexible pad formed for external enwrappment about a patient's limb. The pad includes a plurality of relatively large individual fluid receiving cells adapted to receive and retain sufficient fluid to exert pressure upon the enwrapped limb for a specified period of time. More particularly, the cells are sequentially pressurized starting at the limb extremity and proceeding in the direction of the patient's heart. It is desirable that the sleeve compression pressure proceed smoothly and evenly along the patient's limb from the extremity heartward. Most pressure sleeves currently in use cannot do this. In fact most of them leave continuous pressure gaps between respective sleeve portions. Such is undesirable.

In view of the foregoing it is an object of this invention to provide a compression sleeve for a patient's limb which will provide a smooth pressure flow with no pressure gaps extending completely around the patient's limb.

It is yet another object of this invention to provide a device for use in applying successive compressive pressures against a patient's limb to produce a smooth pumping action from the patient's limb extremity heartward.

It is a still further object of this invention to provide a sleeve for use in applying compressive pressures against a patient's limb wherein the sleeve comprises a plurality of laterally extending separate fluid pressure members arranged longitudinally along the sleeve from a lower portion of the encased limb to the upper portion thereof with the adjacent lateral edge portions of adjacent pressure members being curved upwardly and then downwardly in unison whereby the respective contiguous edges thereof follow each other so that when pressure is sequentially applied from the lowermost pressure members upward there will never be a continuous circumferential pressure gap on any lateral circular portion of the encased limb.

Another object of this invention is to provide a device of the type described in the proceeding object and further wherein the successive pressurization of each pressure member from the lowermost heartward produces a plurality of circumferential spaced radially inward maximum and minimum forces interdigitated with successive pressure members having similar maximum and minimum forces to produce a smooth gap free pressurization from start to finish.

It is a still further object to provide a device as set forth in the foregoing objects which is comfortable for the patient, easily applied to the patient and very simple to produce.

The foregoing and additional objects and advantages of this invention will become more apparent when taken in conjunction with the following detailed description and drawings showing by way of example a preferred embodiment of this invention.

IN THE DRAWINGS

FIG. 1 is a plan view of the compression sleeve of this invention as seen from the outside, that is the side away from the limb it encases, FIG. 2 is a plan view of the compression sleeve of FIG. 1 as seen from the side which contacts the limb it encases, FIG. 3 is a diagrammatic view of the compression sleeve as applied to a limb with the fastening and securing means omitted for sake of clarity, FIG. 4 is a plan view of the compression sleeve of FIG. 1 illustrating relative distribution of the pressure forces shown in FIG. 3 in plan form, FIG. 5 is a sectional view of a more or less conventional compression sleeve comprising a plurality of lateral tubular members which encase the limb and leave pressure gaps between successive tubular members, and FIG. 6 is a plan view of the compression sleeve disclosed in FIG. 1 of Whitney U.S. Pat. No. 4,453,538 which is incorporated herein for disclosure purposes.

DETAILED DESCRIPTION

Figure 1:
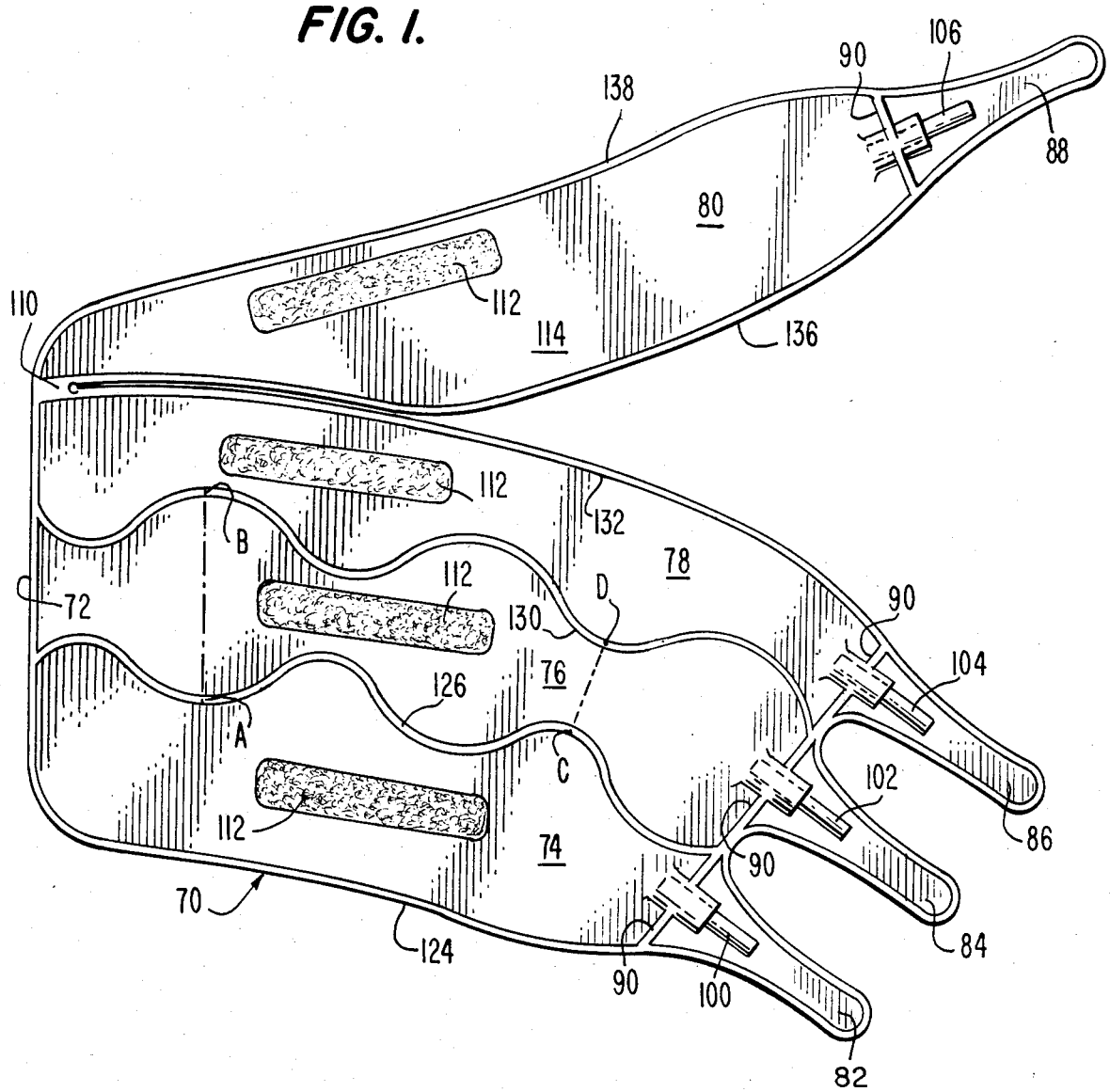

The present invention is an improvement over the compression sleeve illustrated in FIG. 1 of applicant's U.S. Pat. No. 4,453,538 which issued June 12, 1984. Such compression sleeve is shown in FIG. 6 of the drawings in this application.

Figure 5:
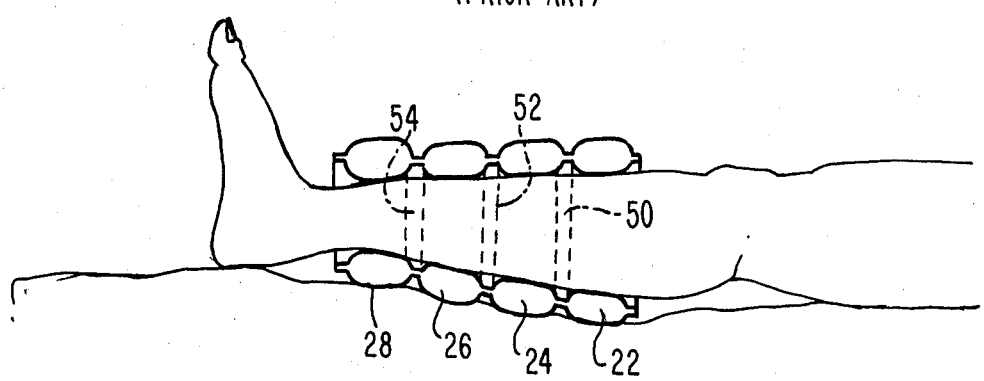
Figure 6:
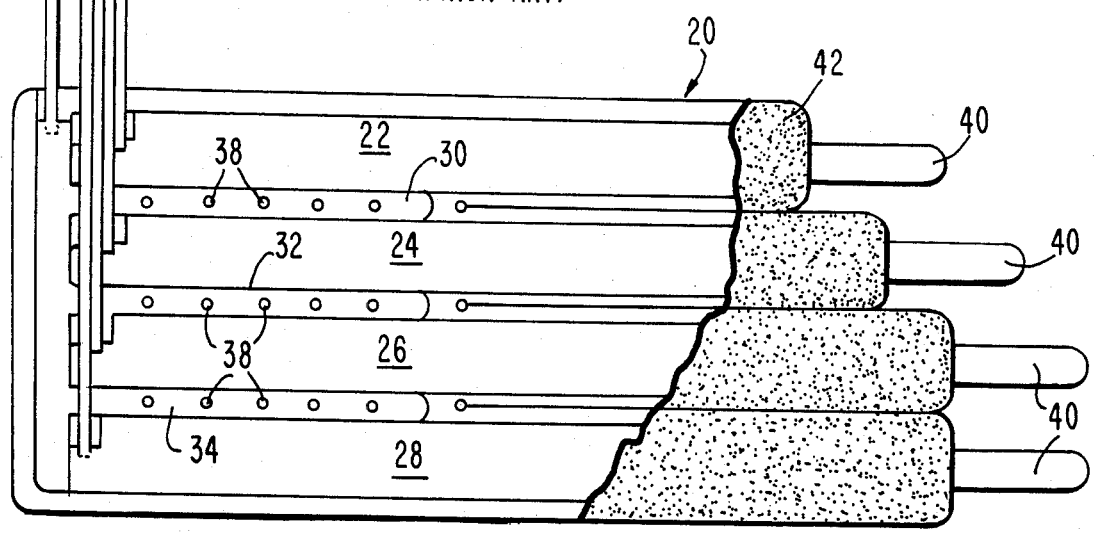

Referring to FIG. 6 of the drawings, compression sleeve 20 comprises a plurality of laterally extending tubular pressure members 22, 24, 26 and 28. A plurality of ventilating tubular members 30, 32 and 34 are positioned between the pressure tubular members. Holes 38 are provided in the ventilating tubular members as shown in FIG. 6. Fastening means 40 are provided for adjustably securing the various pressure tubular members when encasing a patient's limb. The underside of the compression sleeve 20 may be provided with a cushioning material 42 for patient comfort. The pressure members 22, 24, 26 and 28 are fed pressurized fluid in sequential order by means of tubes 46 while the ventilating tubular members 30, 32 and 34 are fed pressurized fluid by tube 48. It should be noted that the pressure members are separated by a distance at least equal to the width of the ventilating tubular member 30, 32 and 34. Thus when the compression sleeve 20 is applied to the patient's limb it would resemble the diagrammatic presentation in FIG. 5 wherein there are pressure gaps 50, 52 and 54 between adjacent pressure members 22, 24, 26 and 28. These pressure gaps extend completely around the limb and constitute a serious problem with respect to needed blood flow through the venous passages in the limb.

This invention is directed to the curing of such deficiency. Referring to FIG. 1 wherein the device of this invention is shown in plan view, the compression sleeve 70 comprises a vertical edge 72 having a plurality of pressure members 74, 76, 78 and 80 extending laterally therefrom. A plurality of flexible tongues 82, 84, 86 and 88 extend laterally from the sealed ends 90 of pressure members 74, 76, 78 and 80 respectively. Fluid pressure feeding and exhausting tubes 100, 102, 104 and 106 are sealingly connected to pressure members 74, 76, 78 and 80 respectively.

Pressure members 74, 76 and 78 are formed as a unitary flat assembly while pressure member 80 is flexibly attached to the unitary flat assembly by means of a hinge 110 connected to the vertical edge 72 at the top of pressure member 78.

Figure 2:
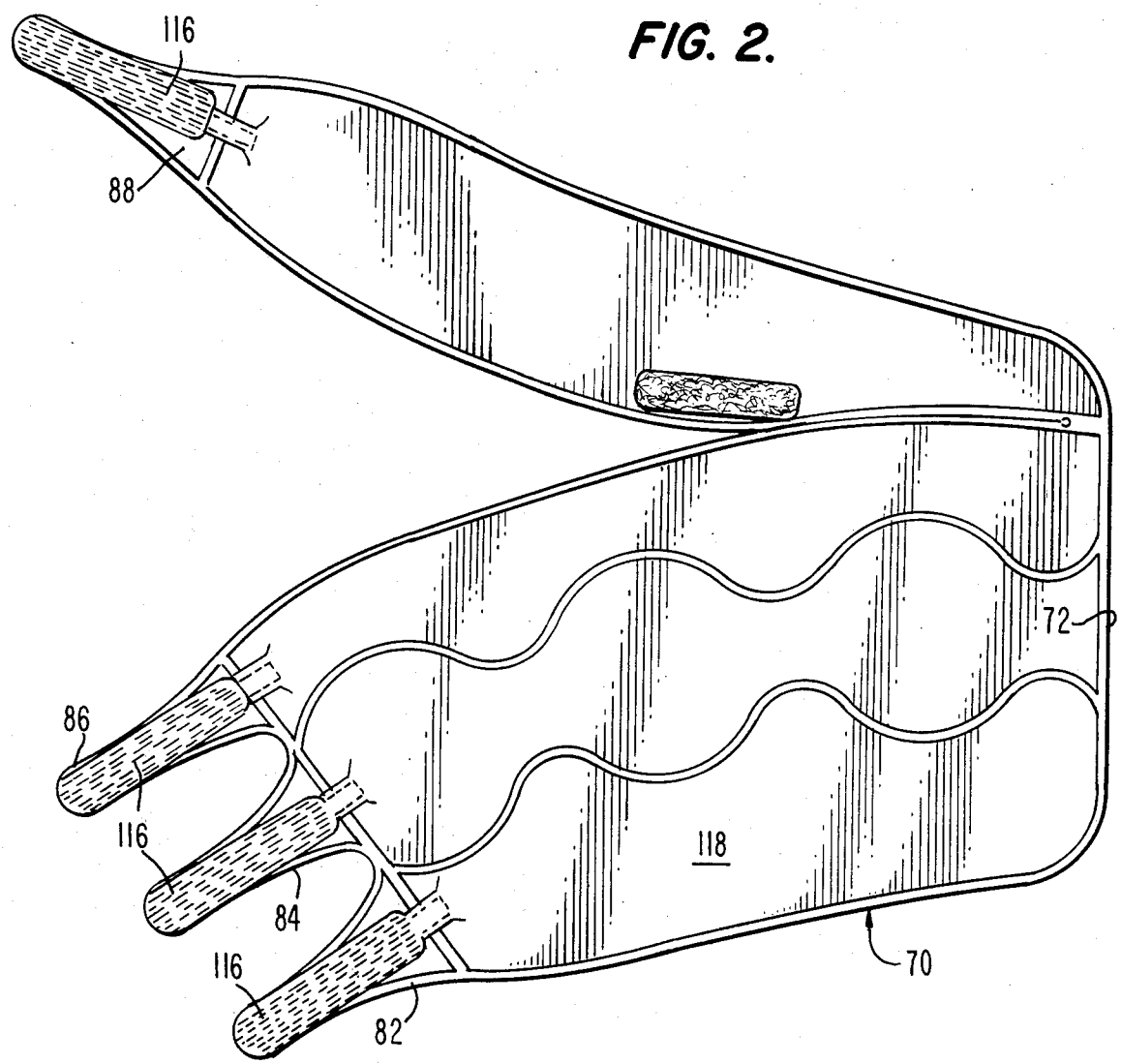

One of the most satisfactory means of fastening the compression sleeve to a limb is by use of Velcro assemblies. In this connection Velcro fastening units 112 are secured to the outside face 114 of each pressure member 74, 76, 78 and 80 as indicated in FIG. 1. The mating Velcro units 116 are attached to tongues 82, 84, 86 and 88 on the inner side 118 of the compression sleeve 70 as shown in FIG. 2.

The configuration of pressure members 74, 76 and 78 is a most important part of this invention. As shown in FIG. 1, pressure member 74 has a lower edge 124 which is generally straight and end edges formed from vertical edge 72 and sealed end 90. The upper edge 126 is wavy having an up and then a down portion somewhat like a sinusoidal curve. The pressure member 76 is formed with vertical edge 72 and sealed end 90 and a lower edge coinciding shape-wise with edge 126 of pressure member 74. The upper edge 130 of pressure member 76 is wavy and generally responds reversely to the configuration of edge 126, that is, where edge 126 curves upwardly edge 130 curves downwardly. More specifically see point A on edge 126 and opposite point B on edge 130, likewise points C and D. Pressure member 78 is defined by edge 130, end edge 72, sealed end 90 and top edge 132 which curves gently between edge 72 and sealed end 90.

Separate pressure member 80 is formed by vertical edge 72, sealed end 90 connected by gently upwardly concave lower edge 136 and upper edge 138.

In use, the compression sleeve 70 is assembled on a limb, such as a leg, by securing the lowermost pressure member 74 around the leg contiguous to the ankle and fastening with Velcro units 116 and 112. Pressure member 76 is next assembled, then pressure member 78 is likewise secured around the proper limb portion. The assembly of these three pressure members about the patient's leg is straight forward. Next comes the pressure member 80 which generally strikes the leg somewhere in the calf area. The pressure member 80 is so arranged about that portion of the leg that its lower edge 136 overlaps upper edge 132 of pressure member 78. See FIG. 3 and overlap 140. Here again the Velcro units 116 and 112 secure the pressure member 80 in this assembled position. If desirable additional fastening means may be provided to retain pressure member 80 in the proper overlapping position.

After checking to make certain that the compression sleeve 70 is properly mounted on the patient's limb the pressure feed tubes 100, 102, 104 and 106 are connected to a sequential pump apparatus along the lines described in U.S. Pat. No. 4,453,538. After which the sequential pumping may commence with pressurization of pressure member 74, then 76, then 78 and lastly 80. After a short retention all pressure members are exhausted and then after a prescribed wait the sequential pressure procedure may again commence. Although pressures and timing may vary over rather wide ranges those disclosed in U.S. Pat. No. 4,453,538 are satisfactory for most purposes.

Figure 3:
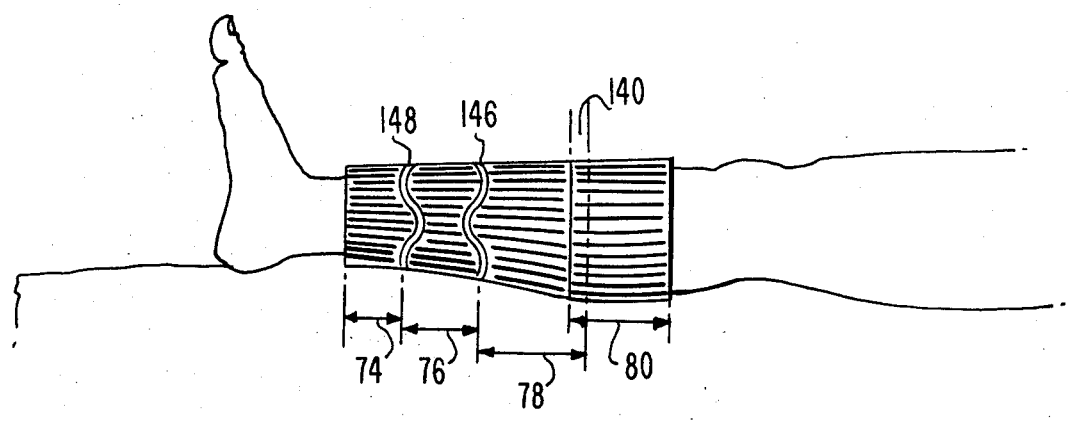

As was stated earlier, one of the important features of this invention is the fact that there are no pressure gaps such as those illustrated in FIG. 5 of the drawings and assigned number 50, 52 and 54. This will be readily apparent when studying FIG. 3 which illustrates, diagramatically, the application of the compression sleeve 70 to the lower leg of a patient. As shown the lowermost pressure member 74 is nearest the ankle area with the remaining pressure members 74, 76 and 80 extending heartward therefrom. The wavy areas 146 and 148 show the heat seal areas defining pressure member 76's upper edge 130 and lower edge 126. Thus the pressure exerted on the limb is as shown by the hatching as shown in FIG. 3. Further, it is readily apparent that there will be no lateral circular pressure gap in the arrangement shown in FIG. 3. The pressure areas of each pressure member are shown in plan form in FIG. 4. This figure makes it evident that there is an interdigitation of pressure areas with regard to pressure members 74, 76 and 78. This view when taken in conjunction with that in FIG. 3 should help in the understanding of the multiple force pumping action produced by the sequential pressurization of the pressure members 74, 76 and 78.

In further explanation of the multiple force pumping arrangement, in the first step, pressure member 74 is pressurized. Note the high points G, H and J and low points K, L and M. These points extend around the patient's limb as shown in FIG. 3. Thus in the first step there are areas between the high points G, H and J which have received no pressure.

Figure 4:
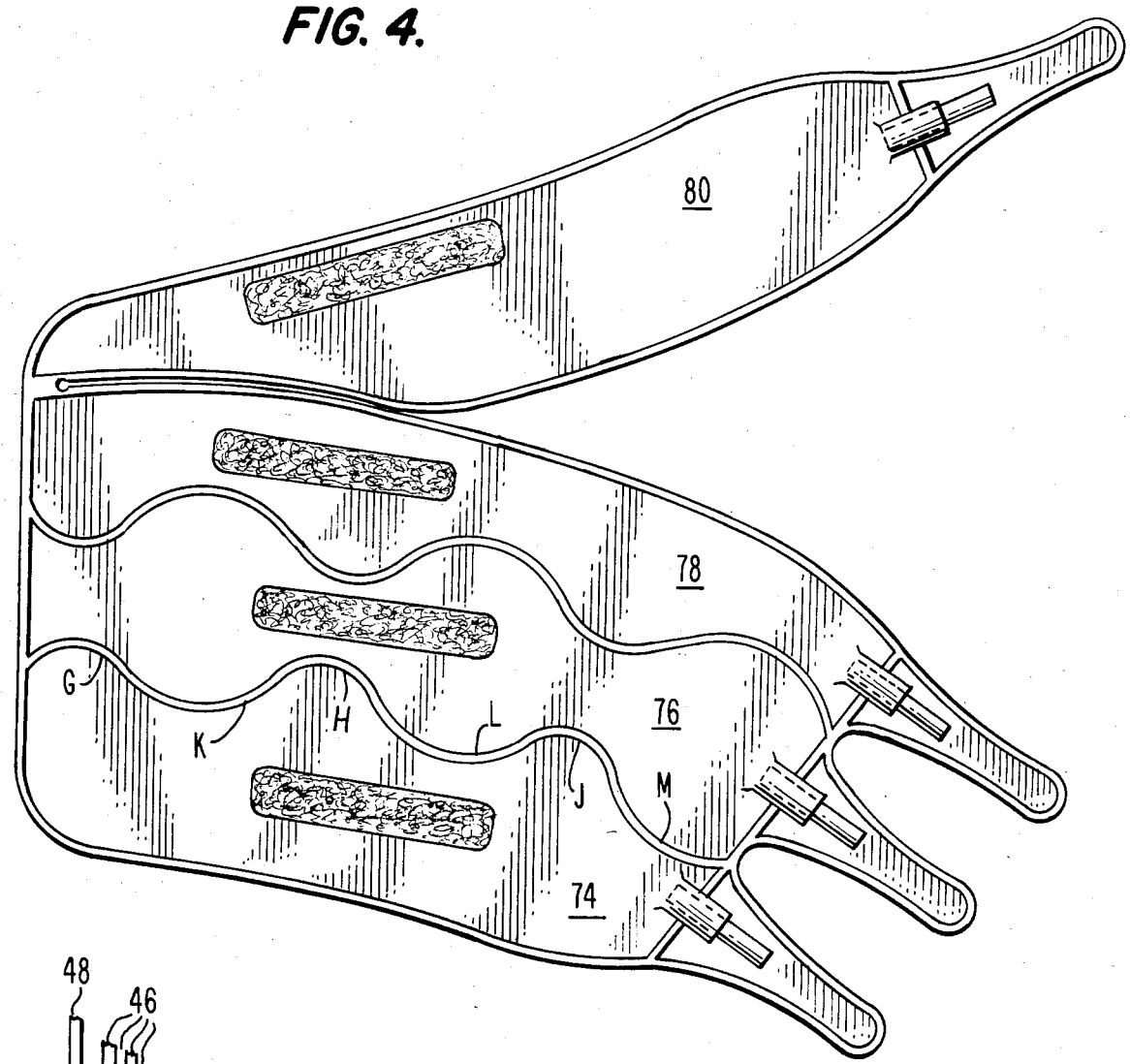

In the second step, pressure member 76 is pressurized in the pattern shown in FIG. 4 so that the areas between high points G, H and J are now filled by the second step pressure. Thus a portion of the patient's limb has received a radially inward force up to point G and H and J in the first step and thus in the second step receives a second force in the area between the points G and H and J. Thus the same lateral circumferential portion of the patient's limb receives two radially inward forces which are displaced circumferentially as indicated by the configuration illustrated in FIG. 4. It is thus readily apparent that there can be no lateral circumferential pressure gaps of the type illustrated in FIG. 5.

Thus the pressure members 74, 76 and 78 produce a sequential pumping action wherein lateral portions of the patient's limb corresponding to the rise and fall of the curved edges of said members receive a two step pressure, one from the peak of the lower pressure member and a second from the valley when fitted by the adjacent pressurized member. Therefore the same venous area of a patient's limb will receive radialy inward pressure in two steps from different circumferential areas. This action takes place between pressure member 74, 76 and 78 in every complete pressurization cycle. As set forth earlier, pressure member 80 overlaps pressure member 78 at the contiguous edge portion so here again there will be no pressure gap between pressure members.

Tests have proven that the compression sleeve 70, as described above, when sequentially pressured will provide a smooth blood flow without any stasis of blood in the limb areas treated.

It was stated earlier in the specification that the compression sleeve 70 was quite easy to produce and such is well supported by the following brief description of one method of making the sleeve 70. First of all take two sheets of heat sealable plastic and heat seal and cut to the configuration of FIG. 1 and then insert and seal in feed tubes and then attach Velcro fastening units. Thus the compression sleeve is ready for use. Other and modified methods of making the sleeve will be readily apparent to those skilled in such art.

What is claimed is:

1. A device for use in applying successive compressive pressures against a patient's limb from a source of pressurized fluid, said device comprising an elongated sleeve adapted for application around a length of a patient's limb, and extending from a lower portion to an upper portion thereof said sleeve having a plurality of laterally extending separate fluid pressure members progressively arranged from a lower portion of the encased limb to the upper portion thereof, each pressure member having lateral edge portions, means to prevent a complete pressure gap around any entire 360° cross sectional portion of the encircled limb, said means including the shaping of adjacent lateral edge portions of adjacent pressure members in substantially an undulating curve and in unison whereby the respective contiguous edges thereof follow each other so that when pressure is sequentially applied from the lowermost pressure member heartward there will never be a pressure gap on any entire 360° cross sectional portion of the encircled limb and means releasably securing the sleeve about the patient's limb with the pressure members encircling the limb.

2. The invention as set forth in claim 1 and wherein the successive pressurization of each pressure member from the lowermost heartward produces a plurality of circumferentially spaced radially inward maximum and minimum forces inter digitated with successive pressure members having similar maximum and minimum forces to produce a smooth stasis free blood flow in the area treated.

3. A device for use in applying sequential compressive pressures against a patient's limb from a source of pressurized fluid said device comprising an elongated sleeve adapted for application around a length of a patient's limb, said sleeve comprising a flat and flexible element having a common vertical side, a plurality of adjacently positioned inflatable pressure member extending laterally from said common vertical side, each pressure member having lateral edges, means to prevent a complete pressure gap around any entire 360° cross sectional portion of the encircled limb, said means including the shaping of adjacent lateral edges of adjacent pressure members (being curved upwardly and downwardly) in substantially an undulating curve in symmetrical manner whereby when the device is applied to the limb of a patient there will never be a pressure gap on any entire 360° cross sectional portion of the encircled limb thereby enhancing operation of the compressive device, and means for releasably securing each respective pressure member when the sleeve is mounted on a patient's limb.

4. The invention as set forth in claim 3 and wherein the successive pressurization of each pressure member from the lowermost heartward produces a plurality of circumferentially spaced radially inward maximum and minimum forces interdigitated with successive pressure members having similar maximum and minimum forces to produce a smooth stasis free blood flow in the area treated.

5. The invention as set forth in claim 3 and wherein there is an additional pressure member flexibly connected to the flat and flexible element at its common vertical side and at the top of the flat and flexible element, said additional member having lateral sides, one of which overlaps the adjacent lateral edge of the adjacent pressure member.

* * * * *